(12) United States Patent
Kobashi et al.

(10) Patent No.: US 11,426,603 B2
(45) Date of Patent: Aug. 30, 2022

(54) RADIATION IRRADIATION PLANNING APPARATUS, CLINICAL DECISION SUPPORT APPARATUS AND PROGRAM

(71) Applicants: HITACHI, LTD., Tokyo (JP); NATIONAL UNIVERSITY CORPORATION HOKKAIDO UNIVERSITY, Sapporo (JP)

(72) Inventors: Keiji Kobashi, Sapporo (JP); Masahiro Mizuta, Sapporo (JP); Hiroyuki Date, Sapporo (JP); Hiroki Shirato, Sapporo (JP); Shinichi Shimizu, Sapporo (JP); Kikuo Umegaki, Sapporo (JP); Shusuke Hirayama, Sapporo (JP); Yusuke Fujii, Tokyo (JP); Toru Umekawa, Tokyo (JP); Rintarou Fujimoto, Tokyo (JP)

(73) Assignees: HITACHI, LTD., Tokyo (JP); NATIONAL UNIVERSITY CORPORATION HOKKAIDO UNIVERSITY, Sapporo (JP)

( * ) Notice: Subject to any disclaimer, the term of this patent is extended or adjusted under 35 U.S.C. 154(b) by 271 days.

(21) Appl. No.: 16/467,504

(22) PCT Filed: Dec. 19, 2016

(86) PCT No.: PCT/JP2016/087808
§ 371 (c)(1),
(2) Date: Jun. 7, 2019

(87) PCT Pub. No.: WO2018/116354
PCT Pub. Date: Jun. 28, 2018

(65) Prior Publication Data
US 2020/0069968 A1 Mar. 5, 2020

(51) Int. Cl.
*A61N 5/10* (2006.01)

(52) U.S. Cl.
CPC ......... *A61N 5/1038* (2013.01); *A61N 5/1037* (2013.01); *A61N 2005/1087* (2013.01)

(58) Field of Classification Search
CPC .............. A61N 5/103–1039; A61N 2005/1041
See application file for complete search history.

(56) References Cited

U.S. PATENT DOCUMENTS 6,222,905 B1    4/2001  Yoda et al.
9,192,782 B1 *  11/2015  Grimm ................ A61N 5/1031
(Continued)

FOREIGN PATENT DOCUMENTS

JP    2000-70389 A      3/2000
JP    3720273 B2       11/2005
(Continued)

OTHER PUBLICATIONS

International Search Report of PCT/JP2016/087808 dated Jan. 31, 2017.

*Primary Examiner* — Thaddeus B Cox
(74) *Attorney, Agent, or Firm* — Mattingly & Malur, PC

(57) ABSTRACT

A treatment planning apparatus 501 or a clinical decision support apparatus 701 calculates a dose distribution, calculates the damage to a normal tissue for a plurality of number of times of radiation irradiation based on the calculated dose distribution, and displays at least one or more calculated damages to the normal tissues on display apparatuses 603 and 703 or outputs the same to an outside of the apparatuses 501 and 701. Accordingly, since effects can be calculated for a plurality of number of times of irradiation, the optimum number of time of irradiation can be presented, and an operator and a doctor can be presented with a suitable decision material of a radiation irradiation planning.

12 Claims, 10 Drawing Sheets

(56) References Cited

U.S. PATENT DOCUMENTS

| | | | |
|---|---|---|---|
| 9,764,162 B1* | 9/2017 | Willcut | A61B 6/5294 |
| 2004/0165696 A1* | 8/2004 | Lee | G16H 30/20 |
| | | | 378/65 |
| 2007/0276777 A1* | 11/2007 | Krishnan | G16H 50/50 |
| | | | 706/46 |
| 2009/0110145 A1* | 4/2009 | Lu | A61N 5/103 |
| | | | 378/65 |
| 2009/0234626 A1* | 9/2009 | Yu | G06N 20/00 |
| | | | 703/11 |
| 2012/0004492 A1* | 1/2012 | Weibrecht | G16H 10/40 |
| | | | 600/1 |
| 2014/0031602 A1 | 1/2014 | Fujimoto et al. | |
| 2016/0016008 A1* | 1/2016 | Kelly | A61N 5/1039 |
| | | | 600/1 |
| 2017/0053562 A1* | 2/2017 | Bova | G09B 23/28 |
| 2018/0148791 A1* | 5/2018 | Scott | C12Q 1/6886 |

FOREIGN PATENT DOCUMENTS

| | | |
|---|---|---|
| JP | 2012-187298 A | 10/2012 |
| JP | 2014-42815 A | 3/2014 |

* cited by examiner

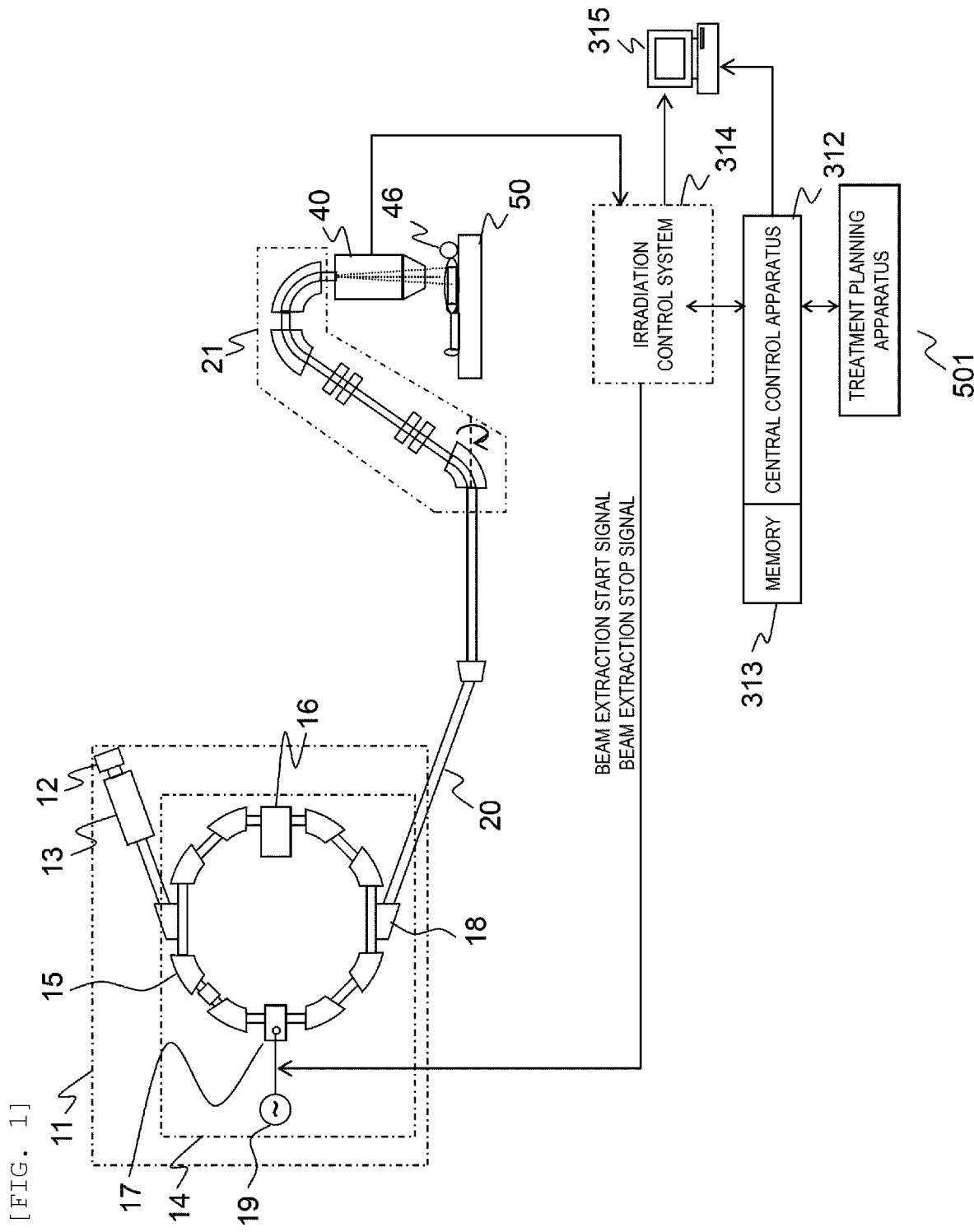
[FIG. 1]

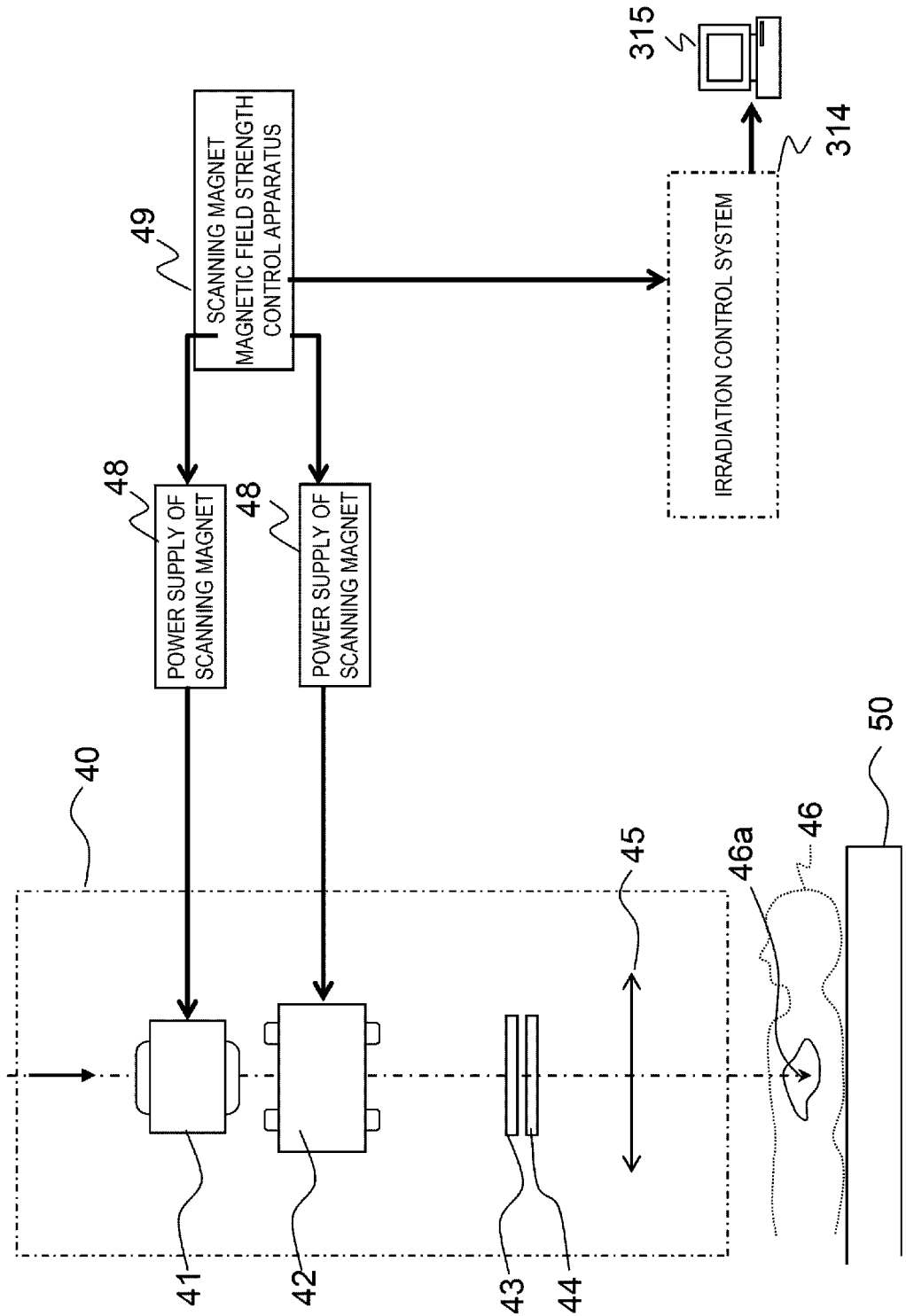

[FIG. 3]
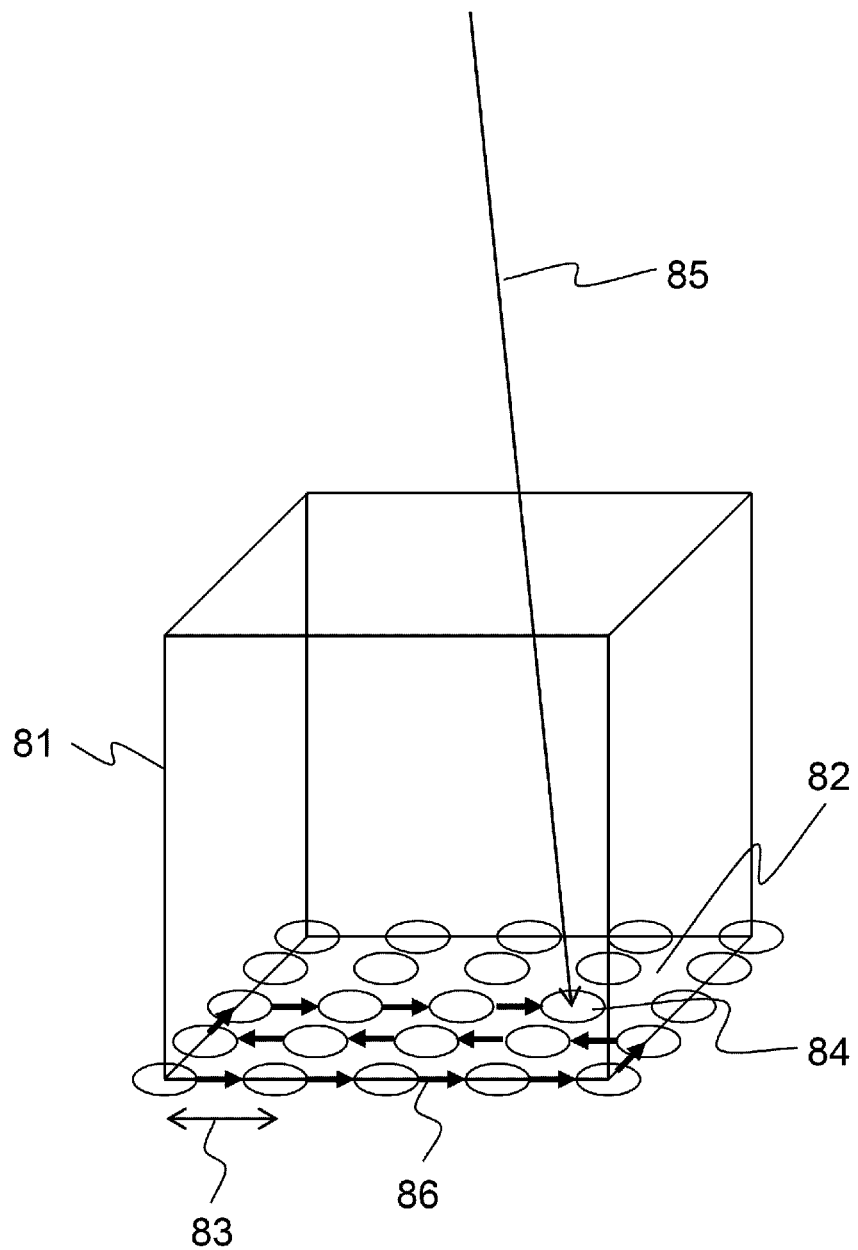

[FIG. 4]
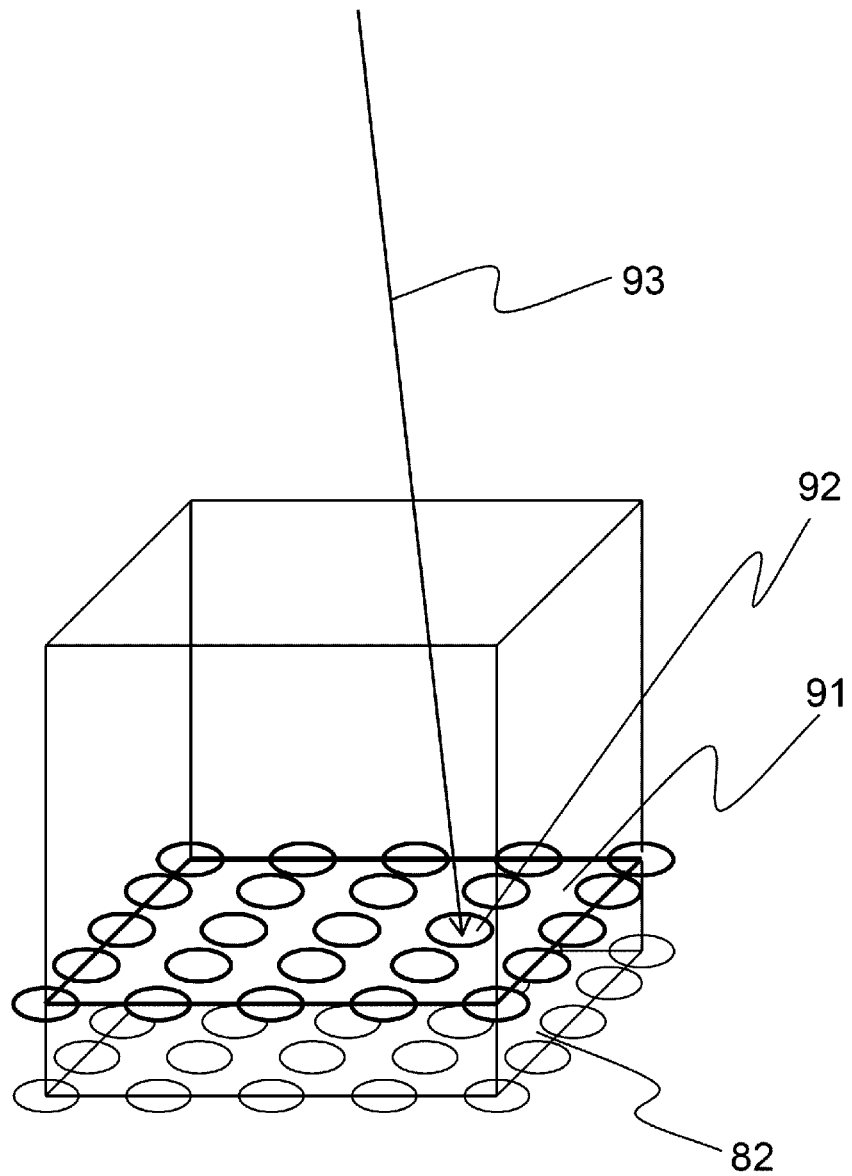

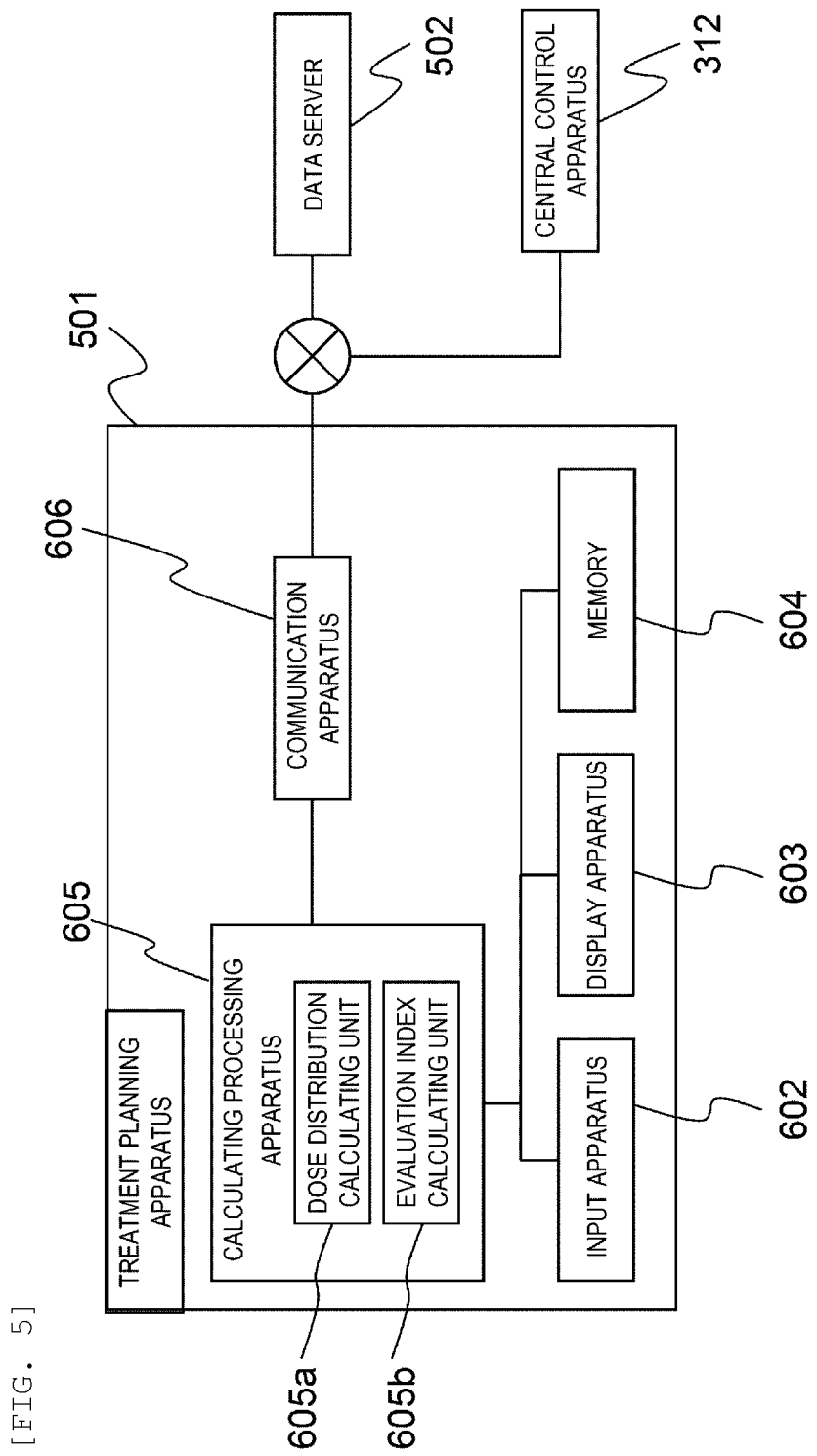
[FIG. 5]

[FIG. 6]
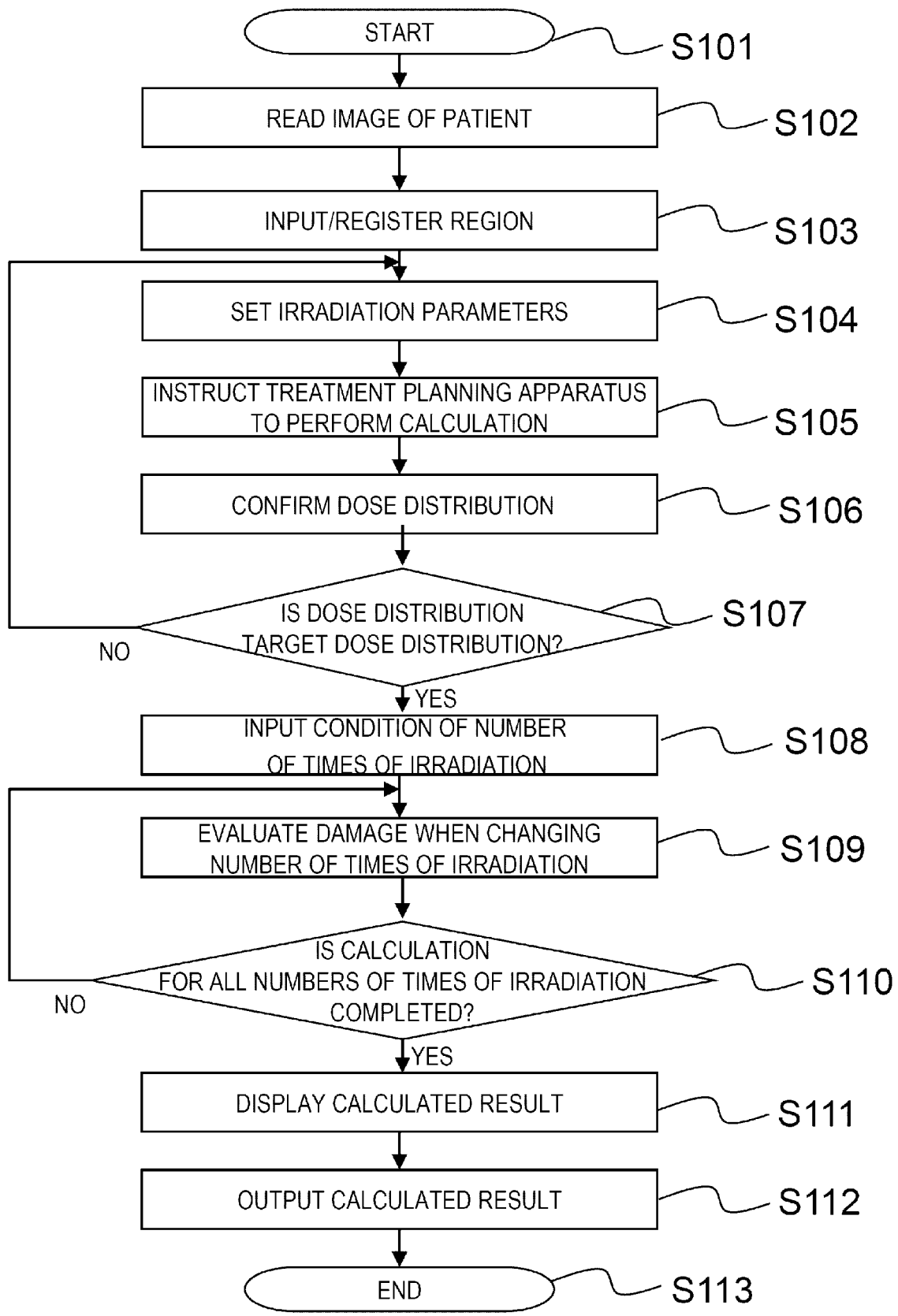

[FIG. 7]
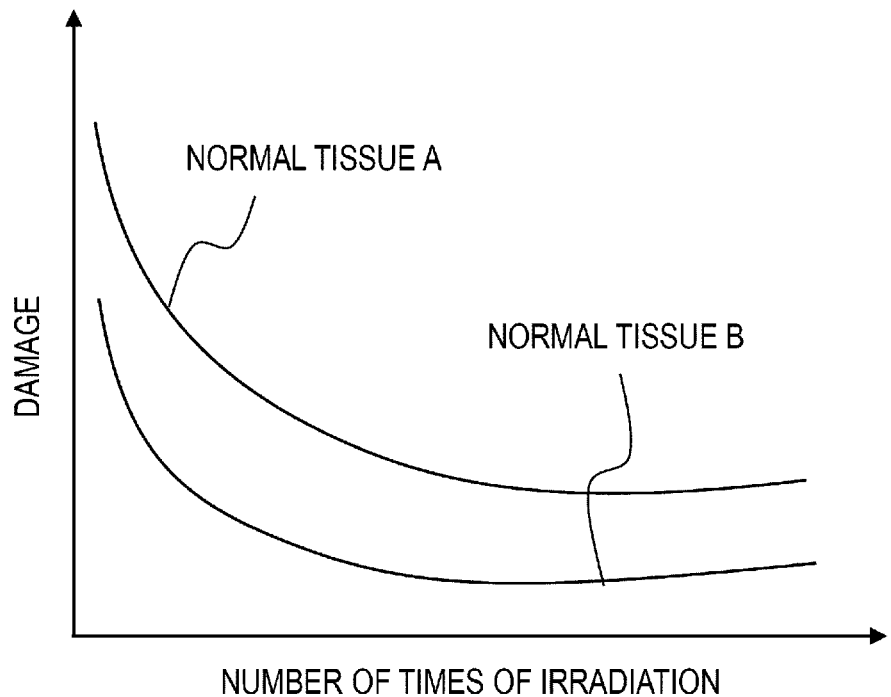
[FIG. 8]
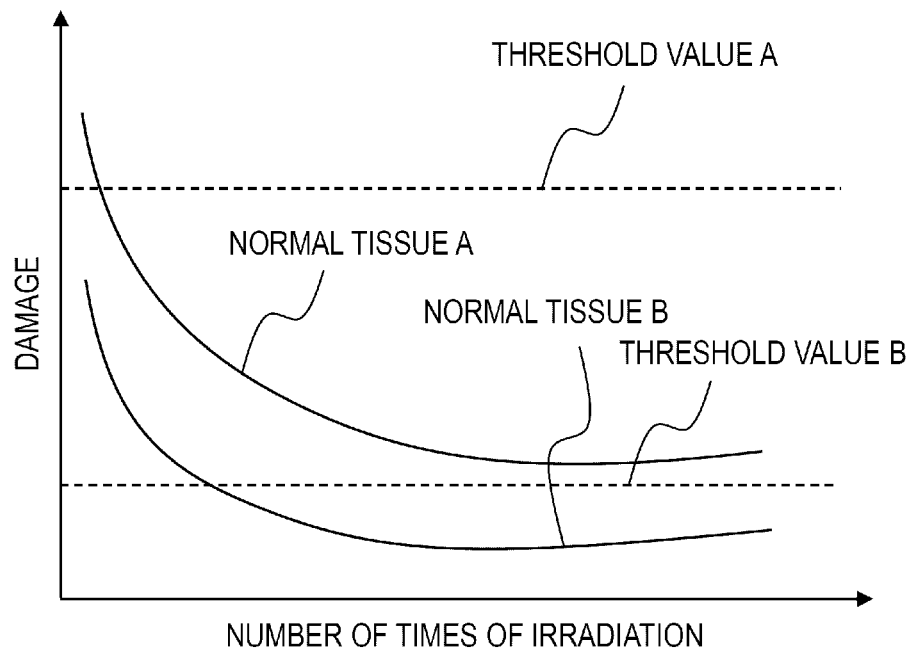

[FIG. 9]
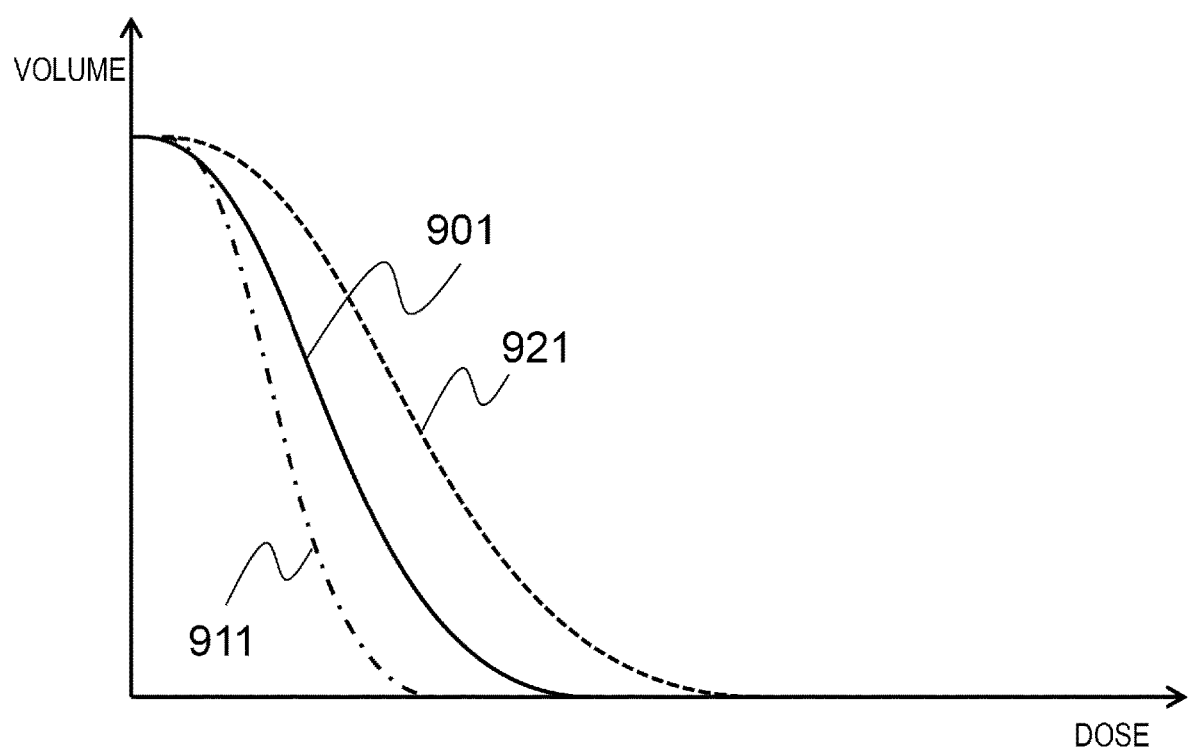

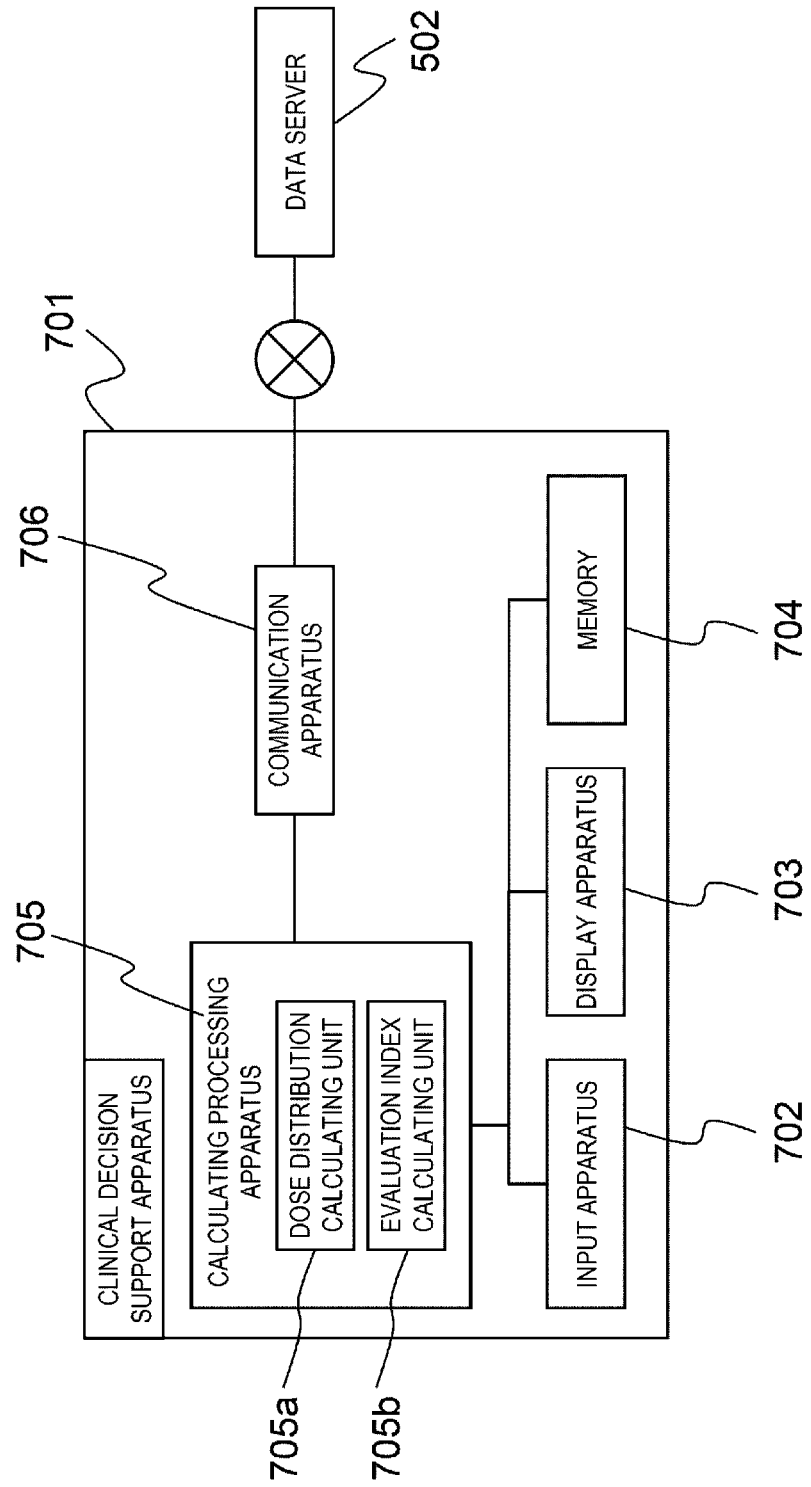
[FIG. 10]

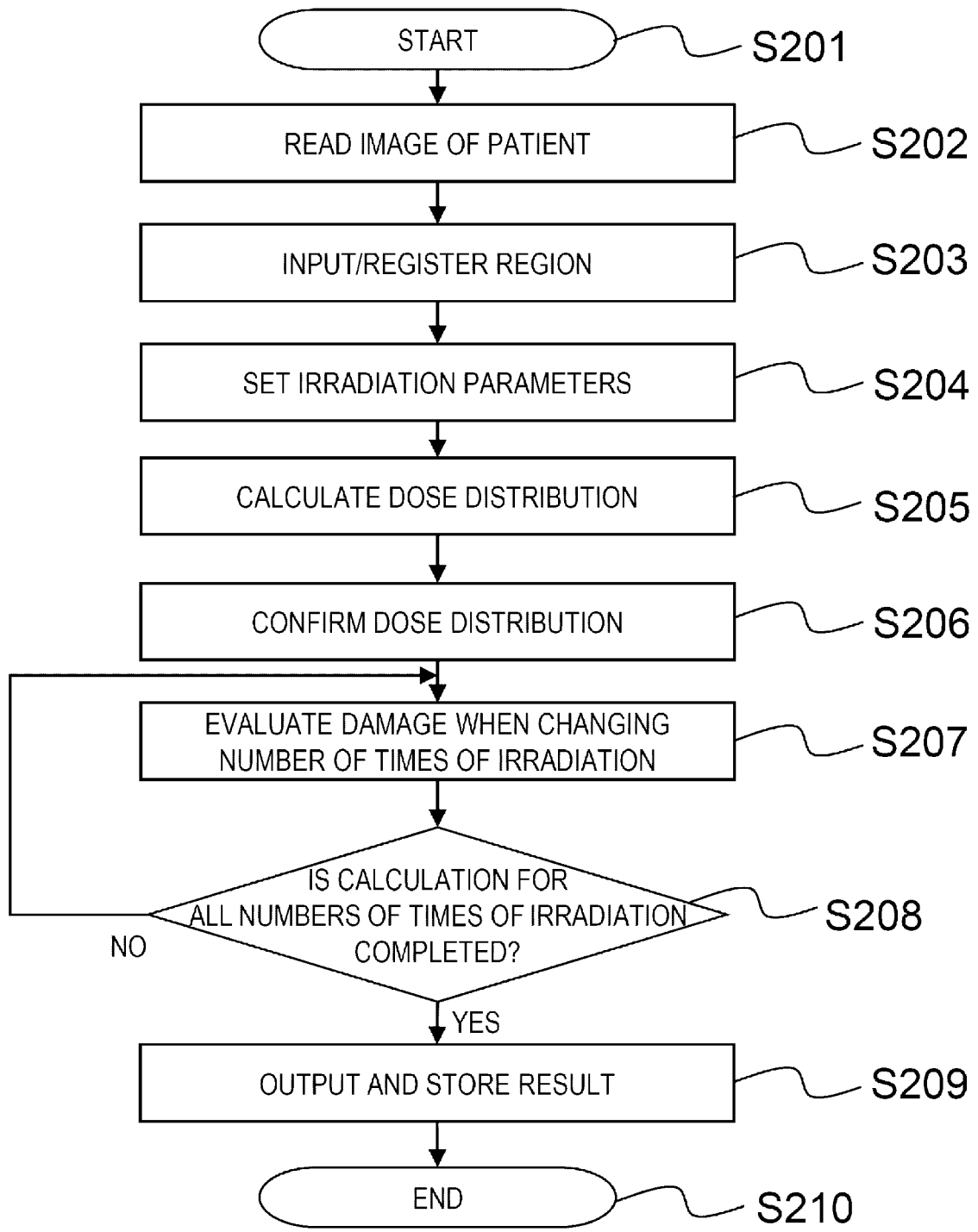
[FIG. 11]

RADIATION IRRADIATION PLANNING APPARATUS, CLINICAL DECISION SUPPORT APPARATUS AND PROGRAM

TECHNICAL FIELD

The present invention relates to a radiation irradiation planning apparatus that makes a treatment planning in a radiotherapy system for treating an affected part such as a tumor with radiation, a clinical decision support apparatus that supports the decision of a doctor on a treatment policy, and a program useful for the above apparatuses.

BACKGROUND ART

In a radiotherapy apparatus in which irradiation parameters change depending on time, for the purpose of performing highly accurate dose distribution calculation based on information on a movement of the affected part included in a 4D CT image, Patent Literature 1 describes a treatment planning apparatus that reads CT images furnished with time information, and calculates a dose distribution by associating the state of an irradiation target corresponding to an elapsed time from the beginning of irradiation with an irradiation position irradiated during the elapsed time.

PRIOR ART LITERATURE

Patent Literature

PTL 1: JP-A-2014-42815

SUMMARY OF INVENTION

Technical Problem

In recent years, radiotherapy aiming at necrotizing tumor cells by irradiation of various radiation rays has been practiced widely. As the radiation ray in use, not only treatments using the most commonly used X-rays but also treatments using particle beams including proton beams are becoming widespread.

The irradiation technique for the radiation ray is highly developed. Progress has been made in the development of techniques for enhancing the dose concentration to the affected part while minimizing the influence on normal tissues around the affected part. In a treatment using X-rays called intensity modulated radiation therapy (IMRT), by performing irradiation from multiple directions while changing a collimator shape, a dose irradiated to the surrounding normal tissues can be minimized even in a case where a complicated shaped target is irradiated. Also used is a method that involves rotating a gantry equipped with an irradiation apparatus to perform irradiation continuously while changing the collimator shape.

Also in the particle therapy, a scanning method is becoming widespread. The method involves irradiating and filling an inside of the tumor with narrow particle beams so that a high dose is applied only to the tumor region.

The radiotherapy requires that detailed makes be previously made with regard to the position to be irradiated with the radiation ray or the state of the affected part. The treatment planning apparatus disclosed in Patent Literature 1 previously determines an irradiation dose and an irradiation position to obtain a desired dose distribution to the affected part and the surroundings of the affected part.

In such radiotherapy, the affected part is irradiated with the radiation ray once a day every several tens of days. In the radiotherapy, a certain degree of the radiation ray is also applied to the normal tissue when the affected part is irradiated with the radiation ray. At this time, irradiation is performed every a plurality of days as described above because of the difference in recovery from the damage caused by the radiation ray in the affected part and the normal tissue. That is, since the normal tissue has a stronger recovering force from the radiation damage than the affected part, the damage to the affected part can be maximized while the damage to the normal tissue is minimized by performing the irradiation for a plurality of times.

In the current radiotherapy, the number of times of irradiation is previously determined for each treatment site and irradiation method, and the predetermined number of times is input to the treatment planning apparatus. Therefore, in the current treatment planning apparatus, a treatment planning is made based on the number of times of irradiation, and there is no technique for evaluating the damage to the normal tissue in a case where the treatment number is changed.

The invention provides a radiation irradiation planning apparatus, a clinical decision support apparatus, and a program with which an effect for a plurality of number of times of times of irradiation can be calculated, and an optimum number of times of irradiation can be presented.

Solution to Problem

In order to solve the above problems, for example, the configurations described in the claims are adopted.

The invention includes a plurality of means for solving the above problems, and an example thereof include a radiation irradiation planning apparatus which creates a radiation irradiation planning, wherein the radiation irradiation planning apparatus calculates a dose distribution formed in the created irradiation planning, calculates an evaluation index of an influence of the radiation ray to a normal tissue for a plurality of number of times of radiation irradiation based on the calculated dose distribution, and displays at least one or more calculated evaluation indexes on a display apparatus or outputs the same from the apparatus.

According to another example, a clinical decision support apparatus that supports a decision of a doctor on a treatment method for a disease, wherein the clinical decision support apparatus calculates a dose distribution in a case where a treatment target is irradiated with a radiation ray, calculates an influence of the radiation ray to a normal tissue for a plurality of number of times of radiation irradiation based on the calculated dose distribution, and displays at least one or more calculated evaluation indexes on a display apparatus or outputs the same from the apparatus.

Advantageous Effect

According to the invention, the effect for a plurality of number of times of irradiation can be calculated, and the optimum number of times of irradiation can be presented.

BRIEF DESCRIPTION OF DRAWINGS

FIG. 1 is a diagram showing an overall particle therapy system suitable for performing a treatment planning created by a treatment planning apparatus of Embodiment 1.

FIG. 2 is a diagram showing an outline of an irradiation planning apparatus according to the particle therapy system of FIG. 1.

FIG. 3 is a diagram showing a concept of spot arrangement of maximum energy in particle irradiation.

FIG. 4 is a diagram showing a concept of spot arrangement of a second energy in the particle irradiation.

FIG. 5 is a block diagram schematically showing the treatment planning apparatus of Embodiment 1.

FIG. 6 is a flowchart showing a flow of making the treatment planning using the treatment planning apparatus of Embodiment 1.

FIG. 7 is a diagram showing an example of a display screen displayed on a display apparatus of the treatment planning apparatus of Embodiment 1.

FIG. 8 is a diagram showing an example of the display screen with a threshold value displayed on the display apparatus of the treatment planning apparatus of Embodiment 1.

FIG. 9 is a diagram showing another example of the display screen displayed on the display apparatus of the treatment planning apparatus of Embodiment 1.

FIG. 10 is a block diagram schematically showing a clinical decision support apparatus of Embodiment 2.

FIG. 11 is a flowchart for performing clinical decision support using the clinical decision support apparatus of Embodiment 2.

DESCRIPTION OF EMBODIMENTS

Embodiments of a radiation irradiation planning apparatus, a clinical decision support apparatus, and a program of the invention will be described below with reference to the drawings.

Embodiment 1

A radiation irradiation planning apparatus according to a preferred embodiment of the invention will be described with reference to FIGS. 1 to 9. First, an overall configuration and an irradiation outline of a particle therapy system suitable for performing a treatment planning created by the radiation irradiation planning apparatus of the present embodiment will be described with reference to FIGS. 1 to 4.

FIG. 1 is a diagram showing an outline of the overall configuration of the particle therapy system.

The present embodiment relates to a radiation irradiation planning apparatus according to an x-ray therapy system or the particle therapy system. In the present embodiment, an irradiation planning apparatus for the particle therapy system that irradiates a proton beam or a heavy particle beam is described as an example of the radiation irradiation planning apparatus, but the similar effect can be obtained by applying the radiation irradiation planning apparatus of the invention to an x-ray therapy system.

In FIG. 1, the particle therapy system includes an ion beam generator 11, a high energy beam transport system 20, a rotating irradiation apparatus 21, a central control apparatus 312, a memory 313, an irradiation control system 314, a display apparatus 315, an irradiation field forming apparatus 40, a bed 50, and a treatment planning apparatus (radiation irradiation planning apparatus) 501.

The ion beam generator 11 includes an ion source 12, a pre-accelerator 13, and a particle beam accelerator 14. In the present embodiment, a synchrotron particle beam accelerator is presumed as the particle beam accelerator 14, but any other particle beam accelerator such as a cyclotron can be used as the particle beam accelerator 14.

As shown in FIG. 1, the synchrotron particle beam accelerator 14 includes bending magnets 15, an acceleration apparatus 16, an extraction radiofrequency acceleration apparatus 17, an extraction deflector 18, and a quadrupole magnet (not shown) on a closed orbit thereof, and includes a radiofrequency power supply 19 outside the closed orbit.

With reference to FIG. 1, a process that a particle beam is generated from the ion beam generator 11 and extracted toward a patient using the synchrotron particle beam accelerator 14 will be described.

First, the particle beam supplied from the ion source 12 are accelerated by the pre-accelerator 13 and sent to the synchrotron as the particle beam accelerator 14. The acceleration apparatus 16 is installed in the synchrotron. A radiofrequency is applied to a radiofrequency acceleration cavity (not shown) provided in the acceleration apparatus 16 in synchronization with a period in which the particle beam circulating in the synchrotron passes through the acceleration apparatus 16 to accelerate the particle beam. In this way, the particle beam is accelerated until a predetermined energy is reached.

After the particle beam is accelerated to the predetermined energy (e.g., 70 MeV to 250 MeV), an extraction start signal is output from the central control apparatus 312 via the irradiation control system 314. Accordingly, the radiofrequency power from the radiofrequency power supply 19 is applied to the particle beam circulating in the synchrotron by an extraction radiofrequency electrode installed in the extraction radiofrequency acceleration apparatus 17, and the particle beam is extracted from the synchrotron.

The high energy beam transport system 20 connects the synchrotron and the irradiation field forming apparatus 40. The particle beam extracted from the particle beam accelerator 14 is guided to the irradiation field forming apparatus 40 installed in the rotating irradiation apparatus 21 via the high energy beam transport system 20.

The rotating irradiation apparatus 21 is an apparatus for irradiating a patient 46 with a beam from any desired direction, and can rotate in any direction around the bed 50 on which the patient 46 is placed by rotating the overall apparatus.

The irradiation field forming apparatus 40 is an apparatus which shapes the shape of the particle beam with which the patient 46 is finally irradiated, and the structure thereof is different depending on an irradiation method. A scattered method and a scanning method are typical irradiation methods, and the invention is effective with both the irradiation methods. The present embodiment will be described using the scanning method.

The scanning method is a method capable of finally forming a high dose region only on the target by irradiating the target directly with a narrow beam transported from the high energy beam transport system 20, and scanning the target three-dimensionally.

Next, the roles and functions of apparatuses in the irradiation field forming apparatus 40 will be briefly described with reference to FIG. 2. FIG. 2 is a diagram showing a configuration of the irradiation field forming apparatus 40 corresponding to the scanning method.

As shown in FIG. 2, the irradiation field forming apparatus 40 includes two scanning magnets 41 and 42, a dose monitor 43, and a beam position monitor 44 from an upstream side.

The dose monitor 43 measures the amount of the particle beam that has passed through the monitor. Meanwhile, the beam position monitor 44 can measure the position where the particle beam has passed. The information from the dose monitor 43 and the beam position monitor 44 enables the irradiation control system 314 to manage that a planned position is irradiated with a planned amount of the beam.

The narrow particle beam transported from the ion beam generator 11 via the high energy beam transport system 20 is deflected in a traveling direction by the scanning magnets 41 and 42. The scanning magnets 41 and 42 are provided such that magnetic lines of force are generated in a direction perpendicular to the traveling direction of the beam, and for example, in FIG. 2, the scanning magnet 41 deflects the beam in a scanning direction 45, and the scanning magnet 42 deflects the beam in a direction perpendicular to scanning direction 45. By using the two scanning magnets 41 and 42, the beam can be moved to any desired position in a plane perpendicular to the traveling direction of the beam, and a target 46a can be irradiated with the beam.

The irradiation control system 314 controls the amount of current to be supplied to the scanning magnets 41 and 42 via a scanning magnet magnetic field strength control apparatus 49. The scanning magnets 41 and 42 are supplied with the current from a power supply of scanning magnet 48, and a magnetic field corresponding to the amount of current is excited, and thereby the amount of deflection of the beam can be freely set. A relationship between the amount of deflection and the amount of current of the particle beam is previously held in the memory 313 of the central control apparatus 312 as a table, and reference is made thereto.

There are two beam scanning methods in the scanning method. One is a discrete method in which the movement and stop of the irradiation position are repeated, and the other is a method in which the irradiation position is changed continuously.

In the discrete method, first, the irradiation is performed with a specified amount of beam while keeping the irradiation position at a certain point. This point is called a spot. After the spot is irradiated with the specified amount of beam, the beam irradiation is temporarily stopped, and then the amount of current of the scanning magnet is changed such that the irradiation can be performed to the next position. After changing the amount of current and moving to the next irradiation position, the irradiation is performed with the beam again.

In the method of continuously moving the irradiation position, the irradiation position is changed while the irradiation is performed with the beam. That is, when the excitation amount of the magnet is continuously changed, the beam is moved while the irradiation is performed with the beam so as to pass through the overall irradiation field. In this method, the change of the irradiation amount for each irradiation position is realized by modulating the scanning speed or the amount of current of the beam, or both.

A conceptual diagram of the irradiation by the discrete method is shown in FIG. 3. FIG. 3 shows an example in which a cube target 81 is irradiated.

Since the particle beam stops at a certain position in the traveling direction and a large portion of energy is applied to the stop position, the energy is adjusted such that a depth at which the beam stops is within or near the target 81. In FIG. 3, a beam having energy which stops near a surface 82 irradiated with the same energy is selected. Discrete beam irradiation positions (spots) are arranged at a spot spacing 83 on the surface. When one spot is irradiated with the specified amount, the beam moves to the next spot. A spot 84 is irradiated with a beam passing through a trajectory 85 of a beam with which the spot 84 is irradiated. When the spots 84 of the same energy arranged within the target 81 are sequentially irradiated, the beam is stopped and the depth thereof is changed, in order to irradiate other depth positions in the target 81.

In order to change the depth at which the beam stops, the energy of the beam irradiated to the patient 46 is changed. One method of changing the energy is to change the setting of the particle beam accelerator 14, that is, the synchrotron in the present embodiment. The particles are accelerated to have the energy set in the synchrotron, and changing the setting allows the energy extracted on the patient 46 to be changed. In this case, since the energy extracted from the synchrotron changes, the energy when passing through the high energy beam transport system 20 also changes, and the setting change of the high energy beam transport system 20 also becomes necessary.

In the example of FIG. 3, the energy is mainly applied to a region corresponding to the surface 82 irradiated with the same energy. By changing the energy, for example, a situation as shown in FIG. 4 is obtained. In FIG. 4, irradiation is performed with a beam having energy lower than the energy used in FIG. 3. Therefore, the beam stops at a shallower position. The surface is represented by a surface 91 irradiated with the same energy. A spot 92, which is one of the spots corresponding to the beam having energy, is irradiated with a beam passing through a trajectory 93 of the beam with which the spot 92 is irradiated.

In this way, when the information on the energy, the irradiation position, and the irradiation amount for each spot is input, the particle therapy system irradiates the target with the particle beam to form a dose distribution. Information on the energy, the irradiation position, and the irradiation amount for each spot is determined by the treatment planning apparatus 501 as shown in FIG. 5.

Next, the treatment planning apparatus (radiation irradiation planning apparatus) 501 which creates an irradiation planning of a radiation ray will be described with reference to FIG. 5. FIG. 5 shows a configuration of the treatment planning apparatus 501 according to a preferred embodiment of the invention.

As shown in FIG. 5, the treatment planning apparatus 501 is connected to a data server 502 and the central control apparatus 312 by a network.

As shown in FIG. 5, the treatment planning apparatus 501 includes an input apparatus 602, a display apparatus 603, a memory 604, a calculating processing apparatus 605, and a communication apparatus 606.

The input apparatus 602 is an apparatus for an operator to input various kinds of information such as a prescribed dose for the target 46a, and the execution, the setting change, and the completion of various kinds of processing when creating a treatment planning, and is, for example, a keyboard or a mouse.

The display apparatus 603 is a display for providing information to the operator when inputting various kinds of information, and the execution, the setting change, and the completion of various kinds of processing necessary in creating the treatment planning.

In particular, on the display apparatus 603 of the present embodiment, treatment planning information created by the calculating processing apparatus 605 to be described later is displayed, and a display screen showing various kinds of information such as the damage to a normal tissue for each number of times of irradiation calculated by an evaluation index calculating unit 605b to be described later (see FIGS. 7 and 8), and a threshold value (maximum value) (see FIG.

8) of the damage allowed for the normal tissue previously input by the input apparatus 602 is displayed. These details will be described later.

The memory 604 is an apparatus that temporarily stores information used in various kinds of calculating processing in the calculating processing apparatus 605 to be described later.

The calculating processing apparatus 605 is an apparatus that performs calculating processing, determines irradiation conditions such that a dose distribution approaches the prescribed dose input by the input apparatus 602, and creates the treatment planning information. In particular, the calculating processing apparatus 605 includes a dose distribution calculating unit 605a that calculates the dose distribution formed in the created irradiation planning, and an evaluation index calculating unit 605b that calculates the damage to the normal tissue for a plurality of number of times of radiation irradiation (evaluation index of the influence of the radiation ray) based on the dose distribution calculated by the dose distribution calculating unit 605a.

The calculating processing apparatus 605 is connected to the input apparatus 602, the display apparatus 603, the memory 604, and the communication apparatus 606, and is connected to the data server 502 via a network. Specifically, the communication apparatus 606 of the treatment planning apparatus 501 is connected to the data server 502 via the network to exchange data relating to the patient.

The calculating processing apparatus 605 of the present embodiment outputs display signals to display, on the display apparatus 603, various kinds of information such as the damage to the normal tissue for each number of times of irradiation calculated by the evaluation index calculating unit 605b, a threshold value (maximum value) of the damage allowed for the normal tissue previously input by the input apparatus 602, and a DVH and dose distribution for a specified number of times of irradiation. In addition, in the calculating processing apparatus 605, the damage to the normal tissue for each normal tissue can be displayed on the display apparatus 603 (see FIG. 8). When there is a plurality of normal tissues, the evaluation index calculating unit 605b can calculate the damage to the normal tissue for each normal tissue.

The calculating processing apparatus 605 can output various kinds of information such as at least one or more damages to the normal tissues calculated by the evaluation index calculating unit 605b to the data server 502 from the treatment planning apparatus 501 via the communication apparatus 606, or output display signals to display various kinds of information such as the damage to the normal tissue on the display apparatus 315 of the particle therapy system.

From here, the flow of making a treatment planning by an operator using the treatment planning apparatus 501 and the flow of the operation/movement of the treatment planning apparatus 501 will be described with reference to FIG. 6. FIG. 6 is a diagram showing a flow of calculation contents performed mainly by the treatment planning apparatus 501 of the present embodiment using the calculating processing apparatus 605.

Before the treatment, an image for the treatment planning is taken. The most commonly used image for the treatment planning is an x-ray computed tomography image (hereinafter referred to as a CT image) taken by a CT apparatus (not shown). The CT image reconstructs three-dimensional data from perspective images acquired from a plurality of directions of the patient.

The CT image taken by the CT apparatus is stored in the data server 502. The treatment planning apparatus 501 uses the CT image.

First, when making of a treatment planning is started (step S101), a technician (or a doctor) who is an operator of the treatment planning apparatus reads target CT data from the data server 502 using an apparatus such as a mouse as the input apparatus 602 (step S102). That is, the treatment planning apparatus 501 copies the CT image from the data server 502 to the memory 604 via the network connected to the communication apparatus 606 by the operation of the input apparatus 602.

When the reading of the three-dimensional CT image from the data server 502 to the memory 604 is completed and the three-dimensional CT image is displayed on the display apparatus 603, the operator confirms the three-dimensional CT image displayed on the display apparatus 603, and meanwhile, the input apparatus 602 is used to input a region to be specified as a target with respect to each of slices of the three-dimensional CT image, that is, each two-dimensional CT image (step S103).

The target to be input here is a region decided to be irradiated with a sufficient amount of the radiation ray because a tumor cell is present or may be present. This is referred to as a target. In a case where there is another region that needs evaluation and control, such as regions where the normal tissue for which the irradiation dose is to be minimized is present near the target, the operator specifies these regions of the normal tissue similarly.

In the region drawing here, the treatment planning apparatus 501 may automatically specify the region based on the region drawing data drawn in the past. In addition, the operator can modify and specify the region automatically drawn by the treatment planning apparatus 501 based on the region drawing data. Alternatively, it may be performed on images of different modalities represented by Magnetic Resonance Imaging (MRI).

Next, the operator sets necessary irradiation parameters so as to create a treatment planning including information on the position and energy of the beam with which the registered target is to be irradiated (step S104). First, the operator sets an irradiation direction. The particle therapy system to which the present embodiment is applied can irradiate the patient with the beam from any desired direction by selecting an angle between the rotating irradiation apparatus 21 and the bed 50. A plurality of irradiation directions can be set for one target. In a case where the irradiation is performed with the beam from a certain direction, it is presumed that the position of a center of gravity of the target 46a coincides with an isocenter (rotating center position of the rotating irradiation apparatus 21) during irradiation as shown in FIG. 2.

Other parameters for irradiation that the operator should determine include a dose value (prescribed dose) to be irradiated and the number of times of irradiation to the region registered in step S102. The prescribed dose includes a dose of radiation with which the target is irradiated and a maximum dose allowed for the normal tissue. The number of times of irradiation determined here is a provisional value used as a base of the calculating processing.

After the above parameters are determined, the treatment planning apparatus 501 automatically performs calculation according to an instruction from the operator (step S105). The details of contents relating to the dose calculation performed by the treatment planning apparatus 501 will be described below.

First, the treatment planning apparatus 501 determines a beam irradiation position. In the case of the above-described discrete scanning method used in the present embodiment, discrete spot positions are calculated. The irradiation position is set so as to cover the target. In a case where a plurality of directions are specified as the irradiation direction (the angle between the rotating irradiation apparatus 21 and the bed 50), the same operation is performed with respect to each direction.

When all the irradiation positions are determined, the calculating processing apparatus 605 of the treatment planning apparatus 501 starts the optimization calculation of the irradiation amount. The irradiation amount to each spot is determined to approach the target prescribed dose set in step S104. In the calculation, a method of using an objective function that quantifies a deviation from a target dose with the irradiation amount for each spot as a parameter is widely adopted. The objective function is defined so as to have a smaller value as the dose distribution satisfies the target dose, and an optimum irradiation amount is calculated by searching for an irradiation amount that minimizes the objective function by repeated calculation.

When the repeated calculation is completed, the irradiation amount necessary for each spot is finally determined. An irradiation order of a plurality of spots is also determined at this stage. Generally, a zigzag path is set as shown by a scan path 86 in FIG. 3, but the irradiation order can be rearranged according to a reference in consideration of a scanning time and a scanning direction.

Next, the treatment planning apparatus 501 calculates the dose distribution by the dose distribution calculating unit 605a of the calculating processing apparatus 605 by using the finally obtained spot position and spot irradiation amount. The calculated result of the dose distribution is displayed on the display apparatus 603 (step S106).

The operator confirms the dose distribution displayed on the display apparatus 603 (step S107). If the dose distribution is not a target dose distribution, the processing returns to step S104, and the setting is changed such as adding the restriction of the dose to a new region. The processing from step S104 to step S107 is repeated until the target dose distribution is obtained. When it is decided that the dose distribution is the target dose distribution, the processing proceeds to step S108.

After the target dose distribution is obtained, the operator inputs information necessary for the search of the number of times of irradiation from the input apparatus 602 so as to evaluate the damage to the normal tissue for each number of times of irradiation, which is a feature of the invention (step S108). The information input in step S108 is a minimum value and a maximum value of the number of times of irradiation to be searched, a target evaluation index, a normal tissue evaluation index, and a threshold value.

Since the normal tissue evaluation index serves as an index of the damage to the normal tissue, it is possible to use a normal tissue complication probability (NTCP), a cell survival rate, and a value obtained by converting the cell survival rate to a dose value with any presumed desired number of times of irradiation. The threshold value specifies a value allowed for each organ with respect to the NTCP and the cell survival rate. These values may be specified each time the treatment planning is created or may be previously determined for each normal tissue. In addition, the value of each normal tissue may be previously recorded for each target position.

After information necessary for the search of the number of times of irradiation is input by the operator and the start of calculation is instructed from the input apparatus 602, the treatment planning apparatus 501 uses the evaluation index calculating unit 605b of the calculating processing apparatus 605 to calculate the damage to the normal tissue for each number of times of irradiation based on the minimum number of times of irradiation instructed by the operator (step S109).

In step S109, the evaluation index calculating unit 605b evaluates the damage to the normal tissue for each number of times of irradiation based on a condition that the effect of the radiation ray on the target 46a is constant. In other words, the damage to the target 46a can be equal to the survival rate of the tumor cells. When the number of times of irradiation is changed under the condition that the effect on the target 46a is constant, the dose value changes, so that it is possible to obtain a dose distribution with equal damage to the target by multiplying the overall dose distribution by a constant. The effect on the target 46a uses the normal tissue evaluation index specified in step S108. Here, for example, a case where the cell survival rate is used will be described as an example.

A representative model for calculating the cell survival rate is a linear quadratic model (LQ) model. In the LQ model, it is known that the survival rate S can be approximated by the equation $S=\exp\{-(\alpha d+\beta d^2)\}$ in a case where the irradiation is performed once. Here, $\alpha$ and $\beta$ are constants depending on the type of the cell, and d is a dose when irradiation is performed with an X-ray. In a case where irradiation is performed with the proton beam as in the present embodiment, assuming the dose of the proton beam is d', the relationship d'=d/1.1 is generally used. Therefore, the survival rate S can be expressed as $S=\exp\{-(1.1\alpha d'+1.21\beta d'^2)\}$ when using the dose d' of the proton beam.

The cell survival rate when the irradiation is performed n times every n days can be expressed as the n-th power of S. In a case where the number of times of irradiation is changed from $n_1$ to $n_2$, and when the dose per irradiation for each number of times of irradiation is $d_1$ and $d_2$, in order to make the effect of the radiation ray on the target equal, it can be expressed as $n_1(1.1\alpha d_1+1.21\beta d_1^2)=n_2(1.1\alpha d_2+1.21\beta d_2^2)$ by setting the logarithms of the survival rates to be equal.

In a case where the treatment planning is firstly made when the number of times of irradiation is $n_1$, by multiplying a dose ratio $d_2/d_1$ obtained from the above equation by the overall dose distribution, it is possible to obtain a dose distribution when the number of times of irradiation is changed while keeping the effect on the target constant.

Here, as the simplest example, description is made by multiplying a dose value of the proton beam by 1.1 times, and using a model in which the effect of irradiating the cells with the radiation ray is equal to the dose of the X-ray. However, strictly speaking, it is known that the effect is different for each energy when the proton beam collides with the cell, and a conversion formula in consideration of the above effects can be used. In addition, the LQ model is a simple model in which the growth effect of the tumor is not taken into consideration, but it is preferable to perform calculation with higher accuracy in consideration of the growth effect.

Depending on the shape of the dose distribution, there are cases where the dose within the target has a distribution shape, that is, there is a low dose location and a high dose location, and the dose applied to the target or normal tissue may not be considered to be constant.

For the dose applied to the target, there is, for example, an index called equivalent uniform dose (EUD) as a dose equivalent to a case where a uniform dose is administered to the target. In addition, there is an index called tumor control probability (TCP) that indicates the probability of all tumor cells being necrotic. The dose ratio $d_2/d_1$ is determined such that these target evaluation indexes are constant, and the dose distribution can be obtained for each number of times of irradiation.

The dose distribution to the target may be formed by a technique called boost that gives a higher dose to a part of the target. In such a case, there is a dose value for irradiating the overall target and a dose value for irradiating a high dose region. To obtain the constant effect on the target, a dose value for the overall target can be adopted, and a dose value for a high dose region can also be adopted.

The influence of the dose distribution thus obtained on the normal tissue is calculated. The cell survival rate can also be calculated according to the LQ model for cells of the normal tissue. For example, as an index (normal tissue evaluation index) indicating the damage, a negative value of the logarithm of the survival rate (−logS) is calculated. However, the values of α and β for each normal tissue are different. It is desirable that α and β for each normal tissue be previously registered in a storage apparatus (not shown) in the treatment planning apparatus 501.

In addition, there are normal tissues whose the maximum dose value is important and whose the average dose value is important for each organ. Therefore, the survival rate can be calculated based on an average value or a maximum value of a predetermined dose distribution for each organ, and a value of −logS can be displayed.

The maximum dose value and the average dose value calculated as described above can be converted into a dose value of the number of times of irradiation specified by the operator and displayed, such that the survival rate becomes equal. The operator can confirm the survival rate as a dose value obtained by converting it into the number of times of irradiation to which the operator is accustomed. Alternatively, NTCP may be used as an index of the damage.

The above calculation is repeated from the minimum value of the number of times of irradiation input in step S108 to the maximum value thereof (step S110).

The calculated result is displayed on the display apparatus 603 of the treatment planning apparatus 501 in a graph as shown in FIG. 7 (step S111).

In the graph displayed on the display apparatus 603, the horizontal axis represents the number of times of irradiation and the vertical axis represents the damage, and a graph is drawn for each normal tissue. Generally, the smaller the number of times of irradiation, the larger the damage to the normal tissue. In addition, when the number of times of irradiation increases, the damage tends to increase slightly.

In addition, the threshold value set in step S108 can be displayed together. A graph which displays the threshold value together is shown in FIG. 8.

As shown in FIG. 8, by showing a threshold value for a normal tissue A and a threshold for a normal tissue B together for each of the normal tissues A and B, the range below the threshold value is the range of the number of times of irradiation allowed for each normal tissue, and thus the number of times of irradiation allowed for each normal tissue can be easily confirmed. In addition, among the minimum allowable number of times of irradiation obtained for each normal tissue, the maximum one is the minimum number of times of irradiation for reducing the damage to the normal tissue below the threshold value. Even in a case where the range is not below the threshold value, the operator can easily confirm the magnitude of the deviation from the threshold value when the number of times of irradiation is changed since the threshold value is shown on the graph.

The operator confirms the damage to the normal tissue for each number of times of irradiation, and uses the input apparatus 602 to determine the number of times of irradiation to be used in the actual treatment. The number of times of irradiation may be the same value as a provisional value of the number of times of irradiation input in step S104, and may be a different value appropriately selected by viewing the graphs shown in FIGS. 7 and 8.

In a case where a different value is selected for the number of times of irradiation, it is necessary to calculate the irradiation amount again because it differs from the irradiation amount calculated in step S105. In a case where the dose value for the target is changed from $d_1$ to $d_2$ by changing the number of times of irradiation, the irradiation amount for each spot can be calculated by multiplying $d_2/d_1$ by the irradiation amount for each spot.

There is a case where the irradiation amount per spot may have a maximum value and a minimum value as restrictions from the irradiation apparatus. In a case where there is a restriction from the irradiation apparatus, it is necessary that the irradiation amounts of all the spots multiplied by a coefficient fall within the restrictions. To fall within the restrictions, the spots larger than or equal to the maximum value are divided into two or more spots, and the spots smaller than or equal to the minimum value are either increased to the minimum value or processed to eliminate the spots. Since the irradiation amount of the spot smaller than or equal to the minimum value changes, the treatment planning apparatus 501 has a function of re-calculating the dose distribution to confirm the distribution and the damage to the normal tissue.

The result thus obtained is transmitted from the treatment planning apparatus 501 to the data server 502 via a network (step S112). Other than the number of times of irradiation, the energy per spot, the irradiation position, and the irradiation amount, the data to be transmitted includes data of a gantry angle, a bed angle, and a positioning image.

By the above operations, the treatment planning apparatus 501 completes the creation of the treatment planning (step S113).

The central control apparatus 312 of the particle irradiation system refers to information from the treatment planning apparatus 501 registered in the data server 502, the patient 46 is positioned at the planned position, and then irradiated with the particle beam according to an instruction of the operator. Such irradiation of the particle beam is repeated for a specified number of times of irradiation.

In the graphs of FIGS. 7 and 8, the damage to the normal tissue is shown as a value. However, the operator uses the input apparatus 602 to specify a number of times of irradiation and the dose distribution calculating unit 605a calculates a dose volume histogram (DVH) or a dose distribution for the specified number of times of irradiation, and thereby the DVH and the dose distribution corresponding to the specified number of times of irradiation can also be displayed on the display apparatus 603 of the treatment planning apparatus 501. An example of displaying the DVH corresponding to the specified number of times of irradiation is shown in FIG. 9.

In FIG. 9, a DVH 901 corresponding to the specified number of times of irradiation is displayed. In such a graph, a DVH 911 for the specified normal tissue is displayed when the specified number of times of irradiation is small, and a DVH 921 is displayed when the specified number of times of irradiation is large. By displaying the DVHs 901, 911 and 921 on the display apparatus 603 and confirming the same, the operator can confirm different DVHs and dose distributions for each number of times of irradiation.

Next, the effects of the present embodiment will be described.

The above treatment planning apparatus 501 which creates a radiation irradiation planning of Embodiment 1 of the invention calculates the dose distribution formed in the created irradiation planning, calculates the damage to the normal tissue for a plurality of number of times of radiation irradiation based on the calculated dose distribution, and displays at least one or more calculated damages to the normal tissues on the display apparatus 603 or outputting the same from the treatment planning apparatus 501.

As a result, since the damage to the normal tissue for each number of times of irradiation becomes clear, it is possible to easily confirm that the planned number of times of irradiation, which is difficult in the related art, is appropriate. In addition, it is possible to know the number of times of irradiation that minimize the damage to the normal tissue, and whether there is room to reduce the number of times of irradiation. That is, the damage to the normal tissue when the number of times of irradiation is changed can be confirmed, and the optimum number of times of irradiation for each patient can be confirmed. In addition, in a case where the number of times of irradiation can be reduced, the burden on the patient can be reduced by reducing the number of times of irradiation. By reducing the number of times of irradiation, the number of people who can be treated by one apparatus can be increased. Even when the number of times of irradiation is not reduced, it is possible to create an irradiation planning in which the damage to the normal tissue can be reduced.

The damage to the normal tissue is calculated under the condition that the effect of the radiation ray on the target 46$a$ is constant. Accordingly, it is possible to shorten the time required for the calculation of the damage to the normal tissue, and it is possible to shorten the time required for the creation of the irradiation planning.

In addition to the damage to the normal tissue, the threshold value of the damage to the normal tissue allowed for the normal tissue is displayed on the display apparatus 603 or output from the treatment planning apparatus 501. Thereby, it is possible to more accurately and easily decide whether the planned number of times of irradiation is appropriate, and whether there is room to reduce the number of times of irradiation.

When there are a plurality of normal tissues, the damage for each normal tissue is displayed on the display apparatus 603 or output from the treatment planning apparatus 501. Thereby, even if there are a plurality of normal tissues, it is possible to select a number of times of irradiation that prioritizes the normal tissue considered important, or to select a number of times of irradiation that minimizes the damage to all normal tissues in total, or to more easily and accurately confirm the optimal number of times of irradiation for each patient.

The DVH or the dose distribution for the specified number of radiation times of irradiation is displayed on the display apparatus 603 or output from the treatment planning apparatus 501. Thereby, the operator can confirm the different DVHs and dose distributions for each number of times of irradiation. Since more decision materials are presented in deciding the optimum number of times of irradiation, it is possible to select a more appropriate number of times of irradiation.

In addition, the apparatus is switched between a mode in which the damage to the normal tissue is displayed on the display apparatus 603 or output from the treatment planning apparatus 501 and a mode in which the number of radiation times of irradiation is automatically determined under the condition that the damage to the normal tissue is previously determined. Thereby, it is possible to reduce the burden on the operator and select the optimal number of times of irradiation.

The treatment planning apparatus of the present embodiment is not limited to the above-described embodiment. In the calculating processing apparatus 605, it is also possible to perform calculation to make the damage to any normal tissue constant and maximize the effect on the target (damage to the target). In this case, the normal tissue and the evaluation index that make the damage constant are specified. Similarly to the case where the effect on the target is constant, the dose distribution is multiplied by a coefficient such that the damage is constant, the damage to each normal tissue is calculated for each number of times of irradiation and the result is displayed on the display apparatus 603. The effect on the target is also calculated for each number of times of irradiation, and the result is displayed on the display apparatus 603 using a similar graph.

Examples of the evaluation index include DVH in addition to the damage to the normal tissue and the effect on the target as described above.

The number of times of irradiation is not only determined by the selection of the operator, but also automatically determined by the treatment planning apparatus 501 based on a preset reference (minimizing the damage to a certain specific normal tissue, minimizing the number of times of irradiation, and minimizing the damage to all normal tissues in total).

In this case, the calculating processing apparatus 605 can switch the treatment planning apparatus between a mode in which the evaluation index of the normal tissue is displayed on the display apparatus 603 or output from the treatment planning apparatus 501 and a mode in which the number of times of radiation irradiation is automatically determined under the condition that the evaluation index is previously determined, by the operation of the input apparatus 602.

In addition, the calculating processing apparatus 605 determines whether the determination is made by the selection of the operator or the determination is automatic in step S108 in FIG. 6 described above, and in a case of the automatic determination, steps S109 and S110 are omitted. After the omitted steps S109 and S110, the processing moves to step S111, and the determined number of times of irradiation can be displayed repeatedly on the display screens as shown in FIGS. 7 and 8. It is also possible to move to step S112 and transmit the calculated result to the data server 502 without displaying.

Embodiment 2

A clinical decision support apparatus and a program according to a preferred embodiment of the invention will be described with reference to FIGS. 10 and 11.

The clinical decision support apparatus is an apparatus that supports the decision of the doctor when determining a treatment method at the clinical site. For example, the clinical decision support apparatus is an apparatus that presents guidelines and past cases to support the decision of the doctor in cases of determining the type and amount of drugs to be administered to patients, specifying disease names, determining treatment methods, or the like.

The present embodiment is directed to a clinical decision support apparatus that supports the decision on a treatment method for a disease to which radiotherapy for cancers or the like may be particularly applied, or a program that is suitably used in an apparatus supporting the decision of the doctor in deciding a treatment method for a disease.

In cancer treatment, in addition to radiotherapy, there are many options such as surgery and chemotherapy, and the doctor selects the treatment method most suitable for the patient from among the options. The clinical decision support apparatus and the program input with the status of the patient show guidelines and past data serving as decision materials of the doctor, and support the decision of the doctor on the treatment policy.

FIG. 10 shows a configuration of a clinical decision support apparatus 701 according to a preferred embodiment of the invention. As shown in FIG. 10, first, the clinical decision support apparatus 701 is connected to the data server 502 via a network.

As shown in FIG. 10, the clinical decision support apparatus 701 includes an input apparatus 702, a display apparatus 703, a memory 704, a calculating processing apparatus 705, and a communication apparatus 706.

The input apparatus 702, the display apparatus 703, the memory 704, and the communication apparatus 706 have substantially the same configuration/operation as the input apparatus 602, the display apparatus 603, the memory 604, and the communication apparatus 606 of the treatment planning apparatus 501 of Embodiment 1 respectively, and will not be described in detail.

The calculating processing apparatus 705 is an apparatus that performs calculating processing, and calculates a dose distribution obtained in a case of irradiating a tumor to be treated with the radiation ray. In particular, the calculating processing apparatus 705 includes a dose distribution calculating unit 705a that calculates a dose distribution in the case where a treatment target is irradiated with the radiation ray, and an evaluation index calculating unit 705b that calculates the damage to the normal tissue for a plurality of number of times of radiation irradiation (evaluation index of the influence of the radiation ray) based on the dose distribution calculated by the dose distribution calculating unit 705a.

The evaluation index calculating unit 705b calculates the damage to the normal tissue under the condition that the effect of the radiation ray on the treatment target is constant. When there are a plurality of normal tissues, the damage to the normal tissue for each normal tissue is calculated. In addition, when calculating the dose distribution, a dose distribution in an irradiation planning in which the irradiation condition is similar to the irradiation condition of the radiation ray to the treatment target is used. Further, the damage to the normal tissue for each type of the radiation ray and each irradiation condition is calculated.

The calculating processing apparatus 705 is connected to the input apparatus 702, the display apparatus 703, the memory 704, and the communication apparatus 706, and is connected to other systems inside and outside a hospital such as the data server 502 and a hospital information system (not shown) via a network.

The calculating processing apparatus 705 of the present embodiment outputs display signals to display, on the display apparatus 703, various kinds of information such as the damage to the normal tissue for each number of times of irradiation calculated by the evaluation index calculating unit 705b, and a threshold value (maximum value) of the damage allowed for the normal tissue previously stored in a storage apparatus (not shown). In the calculating processing apparatus 705, the damage to the normal tissue for each normal tissue can be displayed on the display apparatus 703 (see FIG. 8).

The calculating processing apparatus 705 can also output various kinds of information such as at least one or more calculated damages to the normal tissues calculated by the evaluation index calculating unit 705b to the data server 502 outside the clinical decision support apparatus 701 via the communication apparatus 706, or output display signals to display various kinds of information such as the damage to the normal tissue on a display apparatus outside the clinical decision support apparatus 701.

Next, a process of supporting the decision of the doctor on a treatment policy by the clinical decision support apparatus 701 will be described with reference to the flow of FIG. 11.

The clinical decision support apparatus 701 of the present embodiment has a function referring to the guidelines and the past cases in the case of performing the radiotherapy for cancer patients, and has a function of supporting selection of the radiotherapy.

First, when the doctor registers the radiotherapy as a treatment option in the clinical decision support apparatus 701, the clinical decision support apparatus 701 presents guidelines and past cases. In addition, the start of the search of the number of times of irradiation is input from the input apparatus 702 of the clinical decision support apparatus 701. Based on the input of the start, the clinical decision support apparatus 701 starts searching for the number of irradiation time (step S201).

First, the clinical decision support apparatus 701 reads a CT image of the patient (step S202).

Next, regions of a target and a normal tissue are input on the CT image (step S203). The region input has the similar processing as step S103 in the treatment planning apparatus 501. The region may be specified for each slice, or may be automatically input by the clinical decision support apparatus based on the past cases.

Next, the doctor sets irradiation parameters under the presumption that particle therapy is to be performed (step S204). The irradiation parameters include a gantry angle, a prescribed dose, the number of times of irradiation, a beam type (X-rays, proton beams, and heavy particle beams such as carbon) and a striking method thereof (whether it is IMRT, or single field uniform dose (SFUD)). However, the values can be automatically determined by the clinical decision support apparatus 701 by referring to the past cases in which the size of the treatment site and the size of the target are the same.

The clinical decision support apparatus 701 calculates the dose distribution using the dose distribution calculating unit 705a of the calculating processing apparatus 705 according to the input irradiation parameters (step S205, a first step). In the calculation of the dose distribution in step S205, similarly to step S105 in the treatment planning apparatus 501 shown in FIG. 6, the dose distribution can be calculated as in step S106 by optimizing the irradiation amount, but a predicted dose distribution that can be simply calculated can be obtained.

When a predicted dose distribution is to be obtained, the predicted dose distribution is calculated by extracting those having similar sizes of the site and the target from the dose distributions for the past cases. In a case of actual irradiation, it is necessary to accurately calculate the position and amount of the particle beam emitted by a particle therapy system as shown in FIG. 1 using the treatment planning apparatus 501 as shown in FIG. 5. However, since the accurate calculation by the treatment planning apparatus 501 is not necessary at the stage of determining the treatment method, it is often sufficient to simply calculate only the dose distribution. By using the predicted dose distribution, the computational complexity can be greatly reduced, and the calculated result can be presented in a short time.

The doctor confirms the dose distribution thus calculated on the display apparatus 703 as necessary (step S206).

Using the dose distribution thus calculated, the clinical decision support apparatus 701 uses the evaluation index calculating unit 705b of the calculating processing apparatus 705 to calculate the damage of the normal tissue for each number of times of irradiation by the similar method as that in step S109 shown in FIG. 6 (step S207, a portion of a second step).

When the calculation of the damage to the normal tissue for all numbers of times of irradiation (step S208, a portion of the second step) is completed, the clinical decision support apparatus 701 also displays graphs as shown in FIGS. 7 to 9 (step S209, third step) similar to the case of the treatment planning apparatus 501. In step S209, a graph may be displayed for each type of the radiation ray to be emitted and each striking method thereof.

The doctor confirms the displayed graph (step S210). Based on the confirmation, the doctor decides whether the radiation irradiation is suitable for the treatment, and what type of irradiation ray is preferably emitted in which manner, and thus determines the treatment policy.

Next, the effects of the present embodiment will be described.

The above clinical decision support apparatus 701, which supports the decision of the doctor on the treatment method for the disease according to Embodiment of the invention, calculates the dose distribution in the case where the treatment target is irradiated with the radiation ray, calculates the damage to the normal tissue for a plurality of number of radiation times of irradiation based on the calculated dose distribution, and displays at least one or more calculated evaluation indexes on the display apparatus 703 or outputting the same from the clinical decision support apparatus 701. In addition, the program performed by the clinical decision support apparatus 701 causes the clinical decision support apparatus 701 to perform a step of calculating the dose distribution in the case where the treatment target is irradiated with the radiation ray, a step of calculating the damage to the normal tissue for a plurality of number of times of radiation irradiation based on the calculated dose distribution, and a step of displaying at least one or more calculated evaluation indexes on the display apparatus 703 or outputting the same from the clinical decision support apparatus 701.

Since the clinical decision support apparatus 701 has a function of displaying the damage for each number of times of irradiation as described above, the doctor can previously know the period necessary for the treatment and the effect thereof in the case where the radiotherapy is received when the treatment policy is to be determined. Therefore, it is possible to support the doctor to accurately determine the treatment policy.

In addition, the damage to the normal tissue is calculated under the condition that the effect of the radiation ray on the treatment target is constant, and thereby it is possible to shorten the time required for the calculation of the damage to the normal tissue and to support a quick decision.

Further, in addition to the damage to the normal tissue, the maximum value of the damage allowed for the normal tissue is displayed on the display apparatus 703 or output from the clinical decision support apparatus 701. Thereby, it is possible to more easily decide whether the irradiation can be performed under the condition that the damage for the normal tissue caused by the radiation irradiation is allowed, and to more accurately support the decision of the doctor.

Further, the dose distribution is calculated using the dose distribution in the irradiation planning in which the irradiation condition is similar to the irradiation condition of the radiation ray to the treatment target, and thereby the computational complexity of the dose distribution can be greatly reduced, and the calculated result can be presented in a short time. Therefore, a quick decision can be supported.

Further, the dose distribution is calculated for each of a plurality of radiation irradiation methods suing particle beams, X-rays or the like, and the damage is displayed for each number of times of irradiation. Thereby, the selection of an optimal radiotherapy method can be supported in consideration of an irradiation period, and a more accurate decision can be supported.

Furthermore, when there are a plurality of normal tissues, the damage for each normal tissue is displayed on the display apparatus 703 or output from the clinical decision support apparatus 701, and thereby the influence of the radiation ray on various normal tissues can be more accurately decided, and the determination of the accurate treatment policy can be highly supported.

The clinical decision support apparatus 701 as shown in FIG. 10 may be a single system itself, or may be in the form attached to an existing medical information system such as an electronic medical record system.

[Others]

The invention is not limited to the above embodiments, and includes various modifications. The embodiments described above have been described in detail for easy understanding of the invention, and the invention is not necessarily limited to those including all the configurations described above.

REFERENCE SIGNS LIST

11: ion beam generator
12: ion source
13: pre-accelerator
14: particle beam accelerator
15: bending magnet
16: acceleration apparatus
17: extraction radiofrequency acceleration apparatus
18: extraction deflector
19: radiofrequency power supply
20: high energy beam transport system
21: rotating irradiation apparatus
40: irradiation field forming apparatus
41, 42: scanning magnet
43: dose monitor
44: beam position monitor
45: scanning direction
46: patient
46a, 81: target
48: power supply of scanning magnet
49: scanning magnet magnetic field strength control apparatus
50: bed
82, 91: surface irradiated with same energy
83: spot spacing
84, 92: spot
85: trajectory of beam emitted to spot
86: scan path 93: trajectory
312: central control apparatus
313, 604, 704: memory
314: irradiation control system
315, 603, 703: display apparatus
501: treatment planning apparatus (radiation irradiation planning apparatus)
502: data server
602, 702: input apparatus
605, 705: calculating processing apparatus
605a, 705a: dose distribution calculating unit
605b, 705b: evaluation index calculating unit
606, 706: communication apparatus
701: clinical decision support apparatus

The invention claimed is:

1. A radiation irradiation planning apparatus which creates an irradiation planning of a radiation ray, wherein the radiation irradiation planning apparatus
calculates a dose distribution formed in the created irradiation planning;
after the dose distribution is calculated, calculates an evaluation index of a damage caused by the radiation ray to a normal tissue for each of a plurality of number of times of radiation irradiation based on the calculated dose distribution, the plurality of number of times of radiation irradiation being in a range increasing from a predetermined minimum number to a predetermined maximum number;
displays at least one or more calculated evaluation indexes on a display apparatus or outputs the same from the radiation irradiation planning apparatus; and
is configured to be switched between a mode in which the evaluation index of the normal tissue is displayed on the display apparatus or output to the outside of the radiation irradiation planning apparatus, and a mode in which the number of times of radiation irradiation is automatically determined under a condition that the evaluation index is previously determined.

2. The radiation irradiation planning apparatus according to claim 1, wherein
the evaluation index is calculated under a condition that an effect of the radiation ray on a target is constant.

3. The radiation irradiation planning apparatus according to claim 1, wherein
in addition to the evaluation index, a maximum value of the evaluation index allowed for the normal tissue is displayed on the display apparatus or output to the outside of the apparatus.

4. The radiation irradiation planning apparatus according to claim 1, wherein
when there are a plurality of normal tissues, the evaluation index for each normal tissue is displayed on the display apparatus or output to the outside of the apparatus.

5. The radiation irradiation planning apparatus according to claim 1, wherein
a DVH or the dose distribution for a specified number of times of radiation irradiation is displayed on the display apparatus or output to the outside of the apparatus.

6. A clinical decision support apparatus that supports a decision of a doctor on a treatment method for a disease, wherein
the clinical decision support apparatus
calculates a dose distribution in a case where a treatment target is irradiated with a radiation ray;
after the dose distribution is calculated, calculates an evaluation index of a damage caused by the radiation ray to a normal tissue for each of a plurality of number of times of radiation irradiation based on the calculated dose distribution, the plurality of number of times of radiation irradiation being in a range increasing from a predetermined minimum value to a predetermined maximum value;
displays at least one or more calculated evaluation indexes on a display apparatus or outputs the same to an outside of the clinical decision support apparatus; and
is configured to be switched between a mode in which the evaluation index of the normal tissue is displayed on the display apparatus or output to the outside of the clinical decision support apparatus, and a mode in which the number of times of radiation irradiation is automatically determined under a condition that the evaluation index is previously determined.

7. The clinical decision support apparatus according to claim 6, wherein
the evaluation index is calculated under a condition that an effect of the radiation ray on the treatment target is constant.

8. The clinical decision support apparatus according to claim 6, wherein
in addition to the evaluation index, a maximum value of the evaluation index allowed for the normal tissue is displayed on the display apparatus or output to the outside of the apparatus.

9. The clinical decision support apparatus according to claim 6, wherein
the dose distribution is calculated using a dose distribution in an irradiation planning in which an irradiation condition is similar to an irradiation condition of the radiation ray to the treatment target.

10. The clinical decision support apparatus according to claim 6, wherein
the evaluation index is calculated for each type of the radiation ray and each irradiation condition.

11. The clinical decision support apparatus according to claim 6, wherein
when there are a plurality of normal tissues, the evaluation index for each normal tissue is displayed on the display apparatus or output to the outside of the apparatus.

12. A non-transitory computer readable storage medium storing thereon a program to be executed by an apparatus that supports a decision of a doctor on a treatment method for a disease, wherein the program causes the apparatus that supports the decision of the doctor on the treatment method for the disease to perform:
a first step of calculating a dose distribution in a case where a treatment target is irradiated with a radiation ray;
a second step of, after the dose distribution is calculated, calculating an evaluation index of a damage caused by the radiation ray to a normal tissue for each of a plurality of number of times of radiation irradiation based on the dose distribution calculated in the first step, the plurality of number of times of radiation irradiation being in a range increasing from a predetermined minimum number to a predetermined maximum number;
a third step of displaying at least one or more evaluation indexes calculated in the second step on a display apparatus or outputting the same to an outside of the apparatus that supports the decision of the doctor on the treatment method for the disease; and a fourth step of switching between a mode in which the evaluation index of the normal tissue is displayed on the display apparatus or output to the outside of the apparatus that supports the decision of the doctor on the treatment method for the disease, and a mode in which the number of times of radiation irradiation is automatically determined under a condition that the evaluation index is previously determined.

* * * * *